US007459486B2

(12) United States Patent
Lattner

(10) Patent No.: US 7,459,486 B2
(45) Date of Patent: Dec. 2, 2008

(54) MAKING A METHANOL PRODUCT IN A SLURRY BUBBLE REACTOR

(75) Inventor: James R. Lattner, LaPorte, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 84 days.

(21) Appl. No.: 11/484,306

(22) Filed: Jul. 11, 2006

(65) Prior Publication Data

US 2007/0027221 A1     Feb. 1, 2007

Related U.S. Application Data

(60) Provisional application No. 60/702,974, filed on Jul. 27, 2005.

(51) Int. Cl.
*C07C 27/00*     (2006.01)
(52) U.S. Cl. .................. 518/705; 518/712; 518/726; 518/725; 568/700
(58) Field of Classification Search ................. 518/705, 518/712, 726, 725; 568/700
See application file for complete search history.

(56) References Cited

U.S. PATENT DOCUMENTS

| 5,348,982 | A | 9/1994 | Herbolzheimer et al. |
| 5,600,666 | A | 2/1997 | Hiiro |
| 6,341,136 | B1 | 1/2002 | Hiiro |
| 6,400,855 | B1 | 6/2002 | Li et al. |
| 6,608,114 | B1 | 8/2003 | Heydorn et al. |
| 6,642,280 | B2 * | 11/2003 | Sorensen et al. ............ 518/705 |
| 6,881,759 | B2 * | 4/2005 | Nielsen et al. .............. 518/705 |
| 7,115,669 | B2 * | 10/2006 | Zhang et al. ................ 518/706 |

OTHER PUBLICATIONS

U.P.Veera, K.L.Kataria, J.B.Joshi, Effect of superficail gas velocity on gas hold-up profiles in foaming liquids in bubble column reactors. Chemical Engineering Journal, 2004, 99, 53-58.*
Z.Lu, L.Zhao, Y.Zhao, K.Zhang, Mathematical modeling of low temperature liquid phase methanol synthesis process in a bubble slurry reactor. Huagong Xuebao, 2001, 52(4), 333-337.*
Ogawa T. et al.; "*Direct Dimethyl Ether Synthesis*," Journal of Natural Gas Chemistry, vol. 12, pp.219-227, 2003.
Yang R. et al.; "*In situ DRIFT study of low-temperature methanol synthesis mechanism on Cu/Zno catalysts from $CO_2$-containing syngas using ethanol promoter*," Journal of Catalysis, vol. 228, pp. 23-35, 2004.
Setinc, M. et al.; "*On the kinetics of liquid-phase methanol synthesis over commericalCu/ZnO/$Al_2O_3$catalyst*," Chemical Engineering Science, vol. 54, pp. 3577-3586, 1999.

* cited by examiner

*Primary Examiner*—Daniel M Sullivan
*Assistant Examiner*—Sudhakar Katakam

(57) ABSTRACT

This invention is directed to a process of making a methanol product using a slurry bubble reactor. The reactor is operated in the liquid phase, with catalyst particles being suspended in the liquid. The invention provides for efficient use of heat and recovery of product by feeding cool syngas into the reactor, while maintaining a high degree of backmixing within the reactor. Complex cooling equipment is not required in the reaction process.

18 Claims, 1 Drawing Sheet

MAKING A METHANOL PRODUCT IN A SLURRY BUBBLE REACTOR

CROSS REFERENCE TO RELATED APPLICATIONS

This application claims the benefit of Provisional Application No. 60/702,974 filed Jul. 27, 2005, the disclosure of which is fully incorporated herein by reference.

FIELD OF THE INVENTION

This invention relates to the production of methanol. In particular, this invention relates to the production of methanol using a slurry bubble reactor.

BACKGROUND OF THE INVENTION

Methanol synthesis is a strongly exothermic and equilibrium-limited reaction. Increases in reaction temperature tend to disfavor methanol formation, and tend to deactivate some of the more commonly used copper based catalysts. Thus, controlling the reaction temperature and maintaining favorable equilibrium in the methanol reaction process is important.

In large-scale methanol plants, a gas phase synthesis reactor such as a cooled tubular reactor or a multistage adiabatic reactor is typically used. Because, the reaction to methanol is strongly exothermic, and efficient heat removal is a problem, this limits the range of composition of the feed gas that can be treated in a tubular reactor. For example, CO rich gases are very exothermic and difficult to process. Inefficient heat removal leads to hot zones in the reactor, and the catalyst may deactivate faster. Another problem is by-product formation being promoted at high temperatures. For example the production of ethanol and methyl formate increases at increasing temperatures, and alcohols, esters and ketones are difficult to separate from methanol-water mixtures being withdrawn from the process due to the formation of azeotropes.

Slurry bubble reactors are also used in the manufacture of alcohol. These beds involve bubbling synthesis gas feed into a reactor containing liquid in which methanol synthesis catalyst is maintained in suspension. Methanol is formed as the synthesis gas bubbles up through the liquid and contacts the catalyst.

U.S. Pat. No. 5,348,982 discloses a three phase slurry bubble column reactor. The three gas, liquid and solids phases are determined by the type of chemical reaction in the column. A gas is injected into the slurry bubble column at a velocity so that the solid phase is fluidized while maintaining plug flow over the column length.

U.S. Pat. No. 6,608,114 discloses making methanol using a slurry bubble reactor and dehydrating the methanol to make dimethyl ether. The reactor produces the methanol at relatively low water content to facilitate dimethyl ether formation.

U.S. Pat. No. 6,642,280 discloses a control scheme for conversion of variable composition synthesis gas to liquid fuels in a three-phase or slurry bubble reactor. The control scheme allows constant liquid product production and constant or limited purge gas emission using a variable synthesis gas feed condition. The control scheme provides for adjusting one or more of recycle ratio, water addition, and bypass flow.

U.S. Pat. No. 6,881,759 discloses a liquid phase process for the production of methanol being carried out in a slurry-bed reactor. The methanol product is used as a catalyst suspension liquid medium. The process is cooled using cooling tubes and produces medium or low pressure steam.

The use of slurry bubble columns for methanol or dimethyl ether synthesis typically requires removal of heat from the reactor to control the reaction temperature. Removal of heat from the reactor can be accomplished using a reactor that has sufficient heat transfer surface area and/or a heat transfer medium within the reactor. Tubes, coils, or jackets are examples of heat transfer surface area to transfer heat. Constructing a reactor that contains a slurry of catalyst, as well as provides heat transfer, is complex. What is needed is a process that provides a high level of control of low-temperature slurry bubble column reactors at a relatively low cost.

SUMMARY OF THE INVENTION

This invention provides a process for producing methanol using a slurry bubble reactor. The process provides a high level of temperature control and requires little to no external or internal cooling. In one regard, little to no external cooling is achieved in that use of heat transfer fluid to remove heat from the catalyst is required.

According to one aspect of the invention, there is provided a process for making a methanol product in a slurry bubble reactor. The process comprises feeding synthesis gas (syngas) to a slurry bubble reactor. Preferably, the reactor has a liquid height to diameter ratio of not greater than 10:1.

According to another aspect of the invention, the process for making the methanol product includes separating at least a portion of unreacted synthesis gas components from the methanol product into a concentrated liquid methanol product and a vapor containing syngas. Preferably, at least some of the vapor containing the syngas is recycled back to the reactor at a temperature or volume flow rate to control or maintain the reactor at a predetermined average rector outlet temperature.

In on embodiment of the invention, syngas feed is contacted with methanol forming catalyst in the reactor at a superficial gas velocity of at least 0.05 m/sec to form methanol product. Preferably, the reactor is maintained at an average reactor outlet temperature of not greater than 260° C. Most preferably, the reactor is maintained at an average reactor outlet temperature of not greater than 220° C.

In another embodiment of the invention, the methanol product is continued to form in the reactor until conversion of carbon monoxide in the syngas is at least about 30%. Preferably, the average reactor outlet temperature is further controlled by adjusting the temperature of the feed entering the reactor. In one embodiment, the syngas feed entering the reactor is maintained at an average temperature of not greater than 90° C.

In yet another embodiment, the reactor is maintained at a pressure of not greater than 100 bar absolute. Most preferably, the reactor is maintained at a pressure of not greater than 60 bar absolute.

The methanol forming catalyst that is used can be any catalyst capable of converting the syngas components to methanol. Preferably, the methanol forming catalyst includes an oxide of at least one element selected from the group consisting of copper, silver, zinc, boron, magnesium, aluminum, vanadium, chromium, manganese, gallium, palladium, osmium and zirconium.

In a particularly preferred embodiment, the reactor has a liquid height to diameter ratio of not greater than 5:1. More preferably, the syngas is contacted with the methanol forming catalyst in the reactor at a superficial gas velocity of at least 0.1 μm/sec to form methanol product.

BRIEF DESCRIPTION OF THE DRAWING

An example of one specific embodiment of this invention in shown in the attached FIG. 1, wherein.

DETAILED DESCRIPTION OF THE INVENTION

Figure 1:
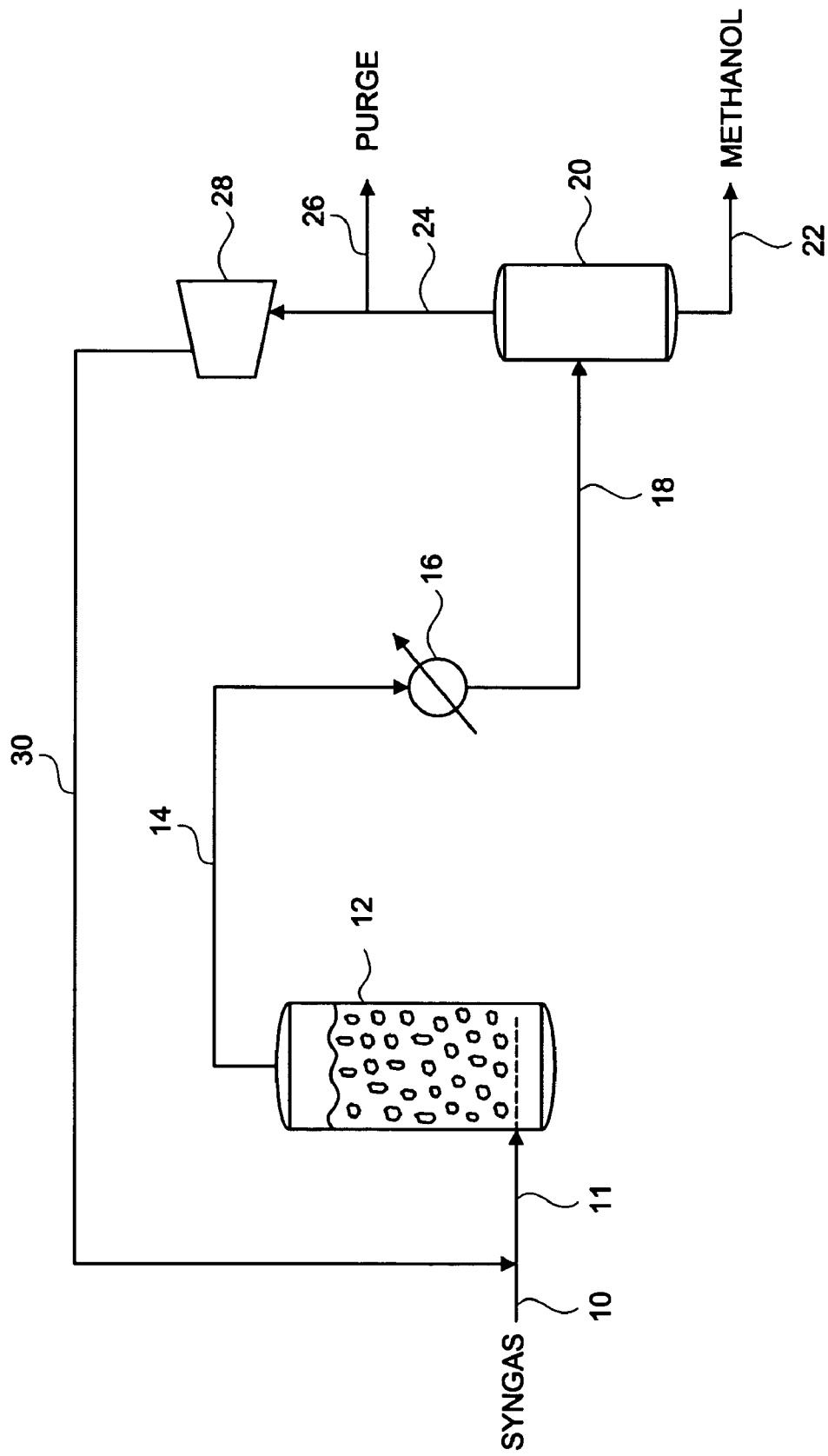
FIG. 1 is a flow diagram of a slurry bubble reactor in which syngas is flowed into the reactor, methanol is recovered and unreacted syngas recovered and recycled as feed.

I. Liquid Phase Slurry Bubble Reaction System

This invention is directed to a process of making a methanol product using a slurry bubble reactor. The reactor is operated in the liquid phase, with catalyst particles being suspended in the liquid. As a synthesis gas (syngas) feed is introduced to the reactor it bubbles through the liquid, contacts the suspended solid catalyst particles, and methanol product is formed. The liquid in which the catalyst particles are suspended is also methanol.

The invention provides for efficient use of heat and recovery of product by feeding cool syngas into the reactor, while maintaining a high degree of backmixing within the reactor. At an appropriate reaction temperature, and with an appropriate degree of backmixing, temperature rises in the reactor, which occurs due to the nature of the exothermic reaction process, can be more favorably controlled. At the appropriate conditions, it is possible to operate the reactor without applying external or internal cooling, or without using a heat transfer fluid to remove heat from the catalyst. So, complex cooling equipment is not required.

The reactor is configured so that there is a high degree of backmixing of liquid, gas and solids (i.e., catalyst) within the reactor. In one embodiment, the reactor has a relatively low liquid height to diameter ratio, with liquid height being the height of the liquid level within the reactor and the diameter being the average diameter of the reactor. Preferably, the reactor has a liquid height to diameter ratio of not greater than 10:1, more preferably not greater than 8:1, and most preferably not greater than 5:1.

The reaction process is also carried out at a relatively high superficial gas velocity (SGV) in order to ensure proper backmixing of liquid, gas and solids (i.e., catalyst) within the reactor. According to this invention, superficial gas velocity is defined as volumetric flow rate of gas into the reactor ($m^3$/sec) divided by the average cross sectional diameter of the reactor ($m^2$). Preferably, the SGV within the reactor is at least 0.05 meters per second (m/sec), preferably at least 0.07 m/sec, and more preferably at least 0.1 cm/sec.

It is preferred in this invention to maintain a relatively low temperature differential between the reactor outlet and the reactor inlet. In general, the lower the differential, the better the backmixing. In one embodiment, the temperature of the reactor is maintained in the reaction process such that the reactor has a temperature differential between the reactor outlet and inlet of not greater than 50° C. Preferably, the reactor has a temperature differential between the reactor outlet and inlet of not greater than 40° C., preferably not greater than 25° C.

In another embodiment of the invention, the reactor is maintained at a relatively low temperature so that the reactor does not require cooling from an outside source, meaning that it is not necessary to use any cooling means external to the reactor vessel to remove heat internal to the reactor vessel. Preferably, the reactor is maintained at a predetermined average reactor temperature. In one embodiment, the reactor is maintained at an average reactor temperature of not greater than 260° C. Preferably, the reactor is maintained at an average reactor outlet temperature of not greater than 250° C., more preferably not greater than 240° C., still more preferably not greater than 230° C., and still most preferably not greater than 220° C.

The reaction is continued in the process until there is sufficient reduction of CO, based on the content of CO fed to the reactor. Preferably, the reaction is progressed in the reactor until conversion of CO is at least about 30%. The reaction is generally continued in the reactor until conversion of CO is from about 30% to about 75%, in particular from about 40% to about 70%.

In one embodiment, the temperature of the reactor is controlled by adjusting the temperature of the feed entering the reactor. Preferably, the temperature of the feed entering the reactor is maintained at an average temperature of not greater than 90° C., more preferably not greater than 75° C., and most preferably not greater than 50° C.

It is preferred to operate the reactor in this invention at relatively low pressures. In one embodiment, the reactor is maintained at a pressure of not greater than 120 bar (absolute). Preferably, the reactor is maintained at a pressure of not greater than 100 bar, and more preferably not greater than 60 bar. In another embodiment, the reactor is maintained at a pressure of from 20 bar to 120 bar. Preferably, the reactor is maintained at a pressure of from 30 bar to 100 bar.

Methanol product that leaves the slurry bubble reactor generally contains unreacted synthesis gas components that can be recovered. In one embodiment the methanol product that leaves the slurry bubble reactor is cooled and at least some of the synthesis gas components are separated from the methanol into at least two streams. Preferably, one stream is a concentrated liquid methanol product, and one stream is a vapor that contains the synthesis gas.

The separated synthesis gas components can be purged, recycled back to the reactor, or a combination of both. In one embodiment of the invention, the separated synthesis gas components that are recycled back to the reactor are cooled and added to the fresh syngas as a make-up gas or added directly to the slurry bubble gas reactor in order to control or maintain the reactor temperature (e.g., the average reactor outlet temperature) at the desired or predetermined level. In another embodiment, the separated synthesis gas components are recycled back to the reactor at a volume flow rate to control or maintain the reaction temperature at the desired or predetermined reactor temperature.

II. Synthesis Gas Production

A. Methods of Making Synthesis Gas Feed

The methanol manufacturing process of this invention uses synthesis gas (syngas) as feed. Synthesis gas comprises carbon monoxide and hydrogen. Optionally, carbon dioxide and nitrogen are included.

Synthesis gas can be manufactured from a variety of carbon sources. Examples of such sources include biomass, natural gas, $C_1$-$C_5$ hydrocarbons, naphtha, heavy petroleum oils, or coke (i.e., coal). Preferably, the hydrocarbon feed stream comprises methane in an amount of at least about 50% by volume, more preferably at least about 70% by volume, most preferably at least about 80% by volume. In one embodiment of this invention natural gas is the preferred hydrocarbon feed source.

One way of converting the carbon source to a methanol product is to first convert the carbon source to synthesis gas (syngas), and then converting the syngas to the methanol using the slurry bubble reactor of this invention. In this invention it is preferred that the syngas is contacted with the methanol forming catalyst in the slurry bubble reactor at a pressure that is not less than 3 bar of that of a syngas forming reactor that is in fluid connection with the slurry bubble reactor. More preferably the syngas is contacted with the methanol forming catalyst in the slurry bubble reactor at a pressure that is not less than 5 bar, and more preferably not less than 10 bar, of that of a syngas forming reactor that is in fluid connection with the slurry bubble reactor.

Any suitable syngas forming reactor or reaction system can be used in combination with the slurry bubble reaction system of this invention. Examples of synthesis gas forming systems include partial oxidation, steam or $CO_2$ reforming, or some combination of these two chemistries.

B. Steam Reforming to Make Syngas

In the catalytic steam reforming process, hydrocarbon feeds are converted to a mixture of $H_2$, CO and $CO_2$ by reacting hydrocarbons with steam over a catalyst. This process involves the following reactions:

$$CH_4 + H_2O \rightleftharpoons CO + 3H_2 \quad (1)$$

or $$C_nH_m + nH_2O \rightleftharpoons nCO + [n+(m/2)]H_2 \quad (2)$$

and $$CO + H_2O \rightleftharpoons CO_2 + H_2 \quad (3) \text{ (shift reaction)}$$

The reaction is carried out in the presence of a catalyst. Any conventional reforming type catalyst can be used. The catalyst used in the step of catalytic steam reforming comprises at least one active metal or metal oxide of Group 6 or Group 8-10 of the Periodic Table of the Elements. The Periodic Table of the Elements referred to herein is that from *CRC Handbook of Chemistry and Physics*, $82^{nd}$ Edition, 2001-2002, CRC Press LLC, which is incorporated herein by reference.

In one embodiment, the catalyst contains at least one Group 6 or Group 8-10 metal, or oxide thereof, having an atomic number of 28 or greater. Specific examples of reforming catalysts that can be used are nickel, nickel oxide, cobalt oxide, chromia and molybdenum oxide. Optionally, the catalyst is employed with at least one promoter. Examples of promoters include alkali and rare earth promoters. Generally, promoted nickel oxide catalysts are preferred.

The amount of Group 6 or Group 8-10 metals in the catalyst can vary. Preferably, the catalyst includes from about 3 wt % to about 40 wt % of at least one Group 6 or Group 8-10 metal, based on total weight of the catalyst. Preferably, the catalyst includes from about 5 wt % to about 25 wt % of at least one Group 6 or Group 8-10 metal, based on total weight of the catalyst.

The reforming catalyst optionally contains one or more metals to suppress carbon deposition during steam reforming. Such metals are selected from the metals of Group 14 and Group 15 of the Periodic Table of the Elements. Preferred Group 14 and Group 15 metals include germanium, tin, lead, arsenic, antimony, and bismuth. Such metals are preferably included in the catalyst in an amount of from about 0.1 wt % to about 30 wt %, based on total weight of nickel in the catalyst.

In a catalyst comprising nickel and/or cobalt there may also be present one or more platinum group metals, which are capable of increasing the activity of the nickel and/or cobalt and of decreasing the tendency to carbon lay-down when reacting steam with hydrocarbons higher than methane. The concentration of such platinum group metal is typically in the range 0.0005 to 0.1% as metal, calculated as the whole catalyst unit. Further, the catalyst, especially in preferred forms, can contain a platinum group metal but no non-noble catalytic component. Such a catalyst is more suitable for the hydrocarbon steam reforming reaction than one containing a platinum group metal on a conventional support because a greater fraction of the active metal is accessible to the reacting gas. A typical content of platinum group metal when used alone is in the range 0.0005 to 0.5% w/w metal, calculated on the whole catalytic unit.

In one embodiment, the reformer unit includes tubes which are packed with solid catalyst granules. Preferably, the solid catalyst granules comprise nickel or other catalytic agents deposited on a suitable inert carrier material. More preferably, the catalyst is NiO supported on calcium aluminate, alumina, spinel type magnesium aluminum oxide or calcium aluminate titanate.

In yet another embodiment, both the hydrocarbon feed stream and the steam are preheated prior to entering the reformer. The hydrocarbon feedstock is preheated up to as high a temperature as is consistent with the avoiding of undesired pyrolysis or other heat deterioration. Since steam reforming is endothermic in nature, and since there are practical limits to the amount of heat that can be added by indirect heating in the reforming zones, preheating of the feed is desired to facilitate the attainment and maintenance of a suitable temperature within the reformer itself. Accordingly, it is desirable to preheat both the hydrocarbon feed and the steam to a temperature of at least 200° C.; preferably at least 400° C. The reforming reaction is generally carried out at a reformer temperature of from about 500° C. to about 1,200° C., preferably from about 800° C. to about 1,100° C., and more preferably from about 900° C. to about 1,050° C.

Gas hourly space velocity in the reformer should be sufficient for providing the desired CO to $CO_2$ balance in the synthesis gas. Preferably, the gas hourly space velocity (based on wet feed) is from about 3,000 per hour to about 10,000 per hour, more preferably from about 4,000 per hour to about 9,000 per hour, and most preferably from about 5,000 per hour to about 8,000 per hour.

Any conventional reformer can be used in the step of catalytic steam reforming. The use of a tubular reformer is preferred. Preferably, the hydrocarbon feed is passed to a tubular reformer together with steam, and the hydrocarbon and steam contact a steam reforming catalyst. In one embodiment, the steam reforming catalyst is disposed in a plurality of furnace tubes that are maintained at an elevated temperature by radiant heat transfer and/or by contact with combustion gases. Fuel, such as a portion of the hydrocarbon feed, is burned in the reformer furnace to externally heat the reformer tubes therein. See, for example, Kirk-Othmer, *Encyclopedia of Chemical Technology*, 3rd Ed., 1990, vol. 12, p. 951; and *Ullmann's Encyclopedia of Industrial Chemistry*, 5th Ed., 1989, vol. A-12, p. 186, the relevant portions of each being fully incorporated herein by reference.

The ratio of steam to hydrocarbon feed will vary depending on the overall conditions in the reformer. The amount of steam employed is influenced by the requirement of avoiding carbon deposition on the catalyst, and by the acceptable methane content of the effluent at the reforming conditions maintained. On this basis, the mole ratio of steam to hydrocarbon feed in the conventional primary reformer unit is preferably from about 1.5:1 to about 5:1, preferably from about 2:1 to about 4:1.

The hydrogen to carbon oxide ratio of the synthesis gas produced will vary depending on the overall conditions of the reformer. Preferably, the molar ratio of hydrogen to carbon oxide in the synthesis gas will range from about 1:1 to about 5:1. More preferably the molar ratio of hydrogen to carbon oxide will range from about 2:1 to about 3:1. Even more preferably the molar ratio of hydrogen to carbon oxide will range from about 2:1 to about 2.5:1. Most preferably the molar ration of hydrogen to carbon oxide will range from about 2:1 to about 2.3:1.

Steam reforming is generally carried out at superatmospheric pressure. The specific operating pressure employed is influenced by the pressure requirements of the subsequent process in which the reformed gas mixture is to be employed. Although any superatmospheric pressure can be used in practicing the invention, pressures of from about 175 psig (1,308 kPa abs.) to about 1,100 psig (7,686 kPa abs.) are desirable. Preferably, steam reforming is carried out at a pressure of from about 300 psig (2,170 kPa abs.) to about 800 psig (5,687 kPa abs.), more preferably from about 350 psig (2,515 kPa abs.) to about 700 psig (4,928 kPa abs.).

C. Partial Oxidation to Make Syngas

The invention further provides for the production of synthesis gas, or CO and $H_2$, by oxidative conversion (also referred to herein as partial oxidation) of hydrocarbon, particularly natural gas and $C_1$-$C_5$ hydrocarbons. According to the process, hydrocarbon is reacted with free-oxygen to form the CO and $H_2$. The process is carried out with or without a catalyst. The use of a catalyst is preferred, preferably with the catalyst containing at least one non-transition or transition metal oxides. The process is essentially exothermic, and is an incomplete combustion reaction, having the following general formula:

$$C_nH_m + (n/2)O_2 \leftrightarrows nCO + (m/2)H_2 \qquad (4)$$

Non-catalytic partial oxidation of hydrocarbons to $H_2$, CO and $CO_2$ is desirably used for producing syngas from heavy fuel oils, primarily in locations where natural gas or lighter hydrocarbons, including naphtha, are unavailable or uneconomical compared to the use of fuel oil or crude oil. The non-catalytic partial oxidation process is carried out by injecting preheated hydrocarbon, oxygen and steam through a burner into a closed combustion chamber. Preferably, the individual components are introduced at a burner where they meet in a diffusion flame, producing oxidation products and heat. In the combustion chamber, partial oxidation of the hydrocarbons generally occurs with less than stoichiometric oxygen at very high temperatures and pressures. Preferably, the components are preheated and pressurized to reduce reaction time. The process preferably occurs at a temperature of from about 1,350° C. to about 1,600° C., and at a pressure of from above atmospheric to about 150 atm.

Catalytic partial oxidation comprises passing a gaseous hydrocarbon mixture, and oxygen, preferably in the form of air, over reduced or unreduced composite catalysts. The reaction is optionally accompanied by the addition of water vapor (steam). When steam is added, the reaction is generally referred to as autothermal reduction. Autothermal reduction is both exothermic and endothermic as a result of adding both oxygen and water.

In the partial oxidation process, the catalyst comprises at least one transition element selected from the group consisting of Ni, Co, Pd, Ru, Rh, Ir, Pt, Os and Fe. Preferably, the catalyst comprises at least one transition element selected from the group consisting of Pd, Pt, and Rh. In another embodiment, preferably the catalyst comprises at least one transition element selected form the group consisting of Ru, Rh, and Ir.

In one embodiment, the partial oxidation catalyst further comprises at least one metal selected from the group consisting of Ti, Zr, Hf, Y, Th, U, Zn, Cd, B, Al, Ti, Si, Sn, Pb, P, Sb, Bi, Mg, Ca, Sr, Ba, Ga, V, and Sc. Also, optionally included in the partial oxidation catalyst is at least one rare earth element selected from the group consisting of La, Ce, Pr, Nd, Pm, Sm, Eu, Gd, Th, Dy, Ho, Er, Tm, Yb and Lu.

In another embodiment the catalyst employed in the process may comprise a wide range of catalytically active components, for example Pd, Pt, Rh, Ir, Os, Ru, Ni, Cr, Co, Ce, La and mixtures thereof. Materials not normally considered to be catalytically active may also be employed as catalysts, for example refractory oxides such as cordierite, mullite, mullite aluminum titanate, zirconia spinels and alumina.

In yet another embodiment, the catalyst is comprised of metals selected from those having atomic number 21 to 29, 40 to 47 and 72 to 79, the metals Sc, Ti V, Cr, Mn, Fe, Co, Ni, Cu, Zr, Nb, Mo, Tc, Ru, Rh, Pd, Ag, Hf, Ta, W, Re, Os Ir, Pt, and Au. The preferred metals are those in Group 8 of the Periodic Table of the Elements, that is Fe, Os, Co, Re, Ir, Pd, Pt, Ni, and Ru.

In another embodiment, the partial oxidation catalyst comprises at least one transition or non-transition metal deposited on a monolith support. The monolith supports are preferably impregnated with a noble metal such as Pt, Pd or Rh, or other transition metals such as Ni, Co, Cr and the like. Desirably, these monolith supports are prepared from solid refractory or ceramic materials such as alumina, zirconia, magnesia, ceria, silica, titania, mixtures thereof, and the like. Mixed refractory oxides, that is refractory oxides comprising at least two cations, may also be employed as carrier materials for the catalyst.

In one embodiment, the catalyst is retained in form of a fixed arrangement. The fixed arrangement generally comprises a fixed bed of catalyst particles. Alternatively, the fixed arrangement comprises the catalyst in the form of a monolith structure. The fixed arrangement may consist of a single monolith structure or, alternatively, may comprise a number of separate monolith structures combined to form the fixed arrangement. A preferred monolith structure comprises a ceramic foam. Suitable ceramic foams for use in the process are available commercially.

In yet another embodiment, the feed comprises methane, and the feed is injected with oxygen into the partial oxidation reformer at a methane to oxygen (i.e., $O_2$) ratio of from about 1.2:1 to about 10:1. Preferably the feed and oxygen are injected into the reformer at a methane to oxygen ratio of from about 1.6:1 to about 8:1, more preferably from about 1.8:1 to about 4:1.

Water may or may not be added to the partial oxidation process. When added, the concentration of water injected into the reformer is not generally greater than about 65 mole %, based on total hydrocarbon and water feed content. Preferably, when water is added, it is added at a water to methane ratio of not greater than 3:1, preferably not greater than 2:1.

The catalyst may or may not be reduced before the catalytic reaction. In one embodiment, the catalyst is reduced and reduction is carried out by passing a gaseous mixture comprising hydrogen and inert gas (e.g., $N_2$, He, or Ar) over the catalyst in a fixed bed reactor at a catalyst reduction pressure of from about 1 atm to about 5 atm, and a catalyst reduction temperature of from about 300° C. to about 700° C. Hydrogen gas is used as a reduction gas, preferably at a concentration of from about 1 mole % to about 100 mole %, based on total amount of reduction gas. Desirably, the reduction is further carried out at a space velocity of reducing gas mixture of from about $10^3$ cm$^3$/g·hr to about $10^5$ cm$^3$/g·hr for a period of from about 0.5 hour to about 20 hours.

In one embodiment, the partial oxidation catalyst is not reduced by hydrogen. When the catalyst is not reduced by hydrogen before the catalytic reaction, the reduction of the catalyst can be effected by passing the hydrocarbon feed and oxygen (or air) over the catalyst at temperature in the range of from about 500° C. to about 900° C. for a period of from about 0.1 hour to about 10 hours.

In the partial oxidation process, carbon monoxide (CO) and hydrogen ($H_2$) are formed as major products, and water and carbon dioxide ($CO_2$) as minor products. The gaseous product stream comprises the above mentioned products, unconverted reactants (i.e. methane or natural gas and oxygen) and components of feed other than reactants.

When water is added in the feed, the $H_2$:CO mole ratio in the product is increased by the shift reaction: $CO+H_2O \leftrightarrows H_2 + CO_2$. This reaction occurs simultaneously with the oxidative conversion of the hydrocarbon in the feed to CO and $H_2$ or synthesis gas. The hydrocarbon used as feed in the partial oxidation process is preferably in the gaseous phase when contacting the catalyst. The partial oxidation process is particularly suitable for the partial oxidation of methane, natural gas, associated gas or other sources of light hydrocarbons. In this respect, the term "light hydrocarbons" is a reference to hydrocarbons having from 1 to 5 carbon atoms. The process may be advantageously applied in the conversion of gas from naturally occurring reserves of methane which contain substantial amounts of carbon dioxide. In one embodiment, the hydrocarbon feed preferably contains from about 10 mole % to about 90 mole % methane, based on total feed content. More preferably, the hydrocarbon feed contains from about 20 mole % to about 80 mole % methane, based on total feed content. In another embodiment, the feed comprises methane in an amount of at least 50% by volume, more preferably at least 70% by volume, and most preferably at least 80% by volume.

In one embodiment of the invention, the hydrocarbon feedstock is contacted with the catalyst in a mixture with an oxygen-containing gas. Air is suitable for use as the oxygen-containing gas. Substantially pure oxygen as the oxygen-containing gas is preferred on occasions where there is a need to avoid handling large amounts of inert gas such as nitrogen. The feed optionally comprises steam.

In another embodiment of the invention, the hydrocarbon feedstock and the oxygen-containing gas are preferably present in the feed in such amounts as to give an oxygen-to-carbon ratio in the range of from about 0.3:1 to about 0.8:1, more preferably, in the range of from about 0.45:1 to about 0.75:1. References herein to the oxygen-to-carbon ratio refer to the ratio of oxygen in the from of oxygen molecules ($O_2$) to carbon atoms present in the hydrocarbon feedstock. Preferably, the oxygen-to-carbon ratio is in the range of from about 0.45:1 to about 0.65:1, with oxygen-to-carbon ratios in the region of the stoichiometric ratio of 0.5:1, that is ratios in the range of from about 0.45:1 to about 0.65:1, being more preferred. When steam is present in the feed, the steam-to-carbon ratio is not greater than about 3.0:1, more preferably not greater than about 2.0:1. The hydrocarbon feedstock, the oxygen-containing gas and steam, if present, are preferably well mixed prior to being contacted with the catalyst.

The partial oxidation process is operable over a wide range of pressures. For applications on a commercial scale, elevated pressures, that is pressures significantly above atmospheric pressure, are preferred. In one embodiment, the partial oxidation process is operated at pressures of greater than atmospheric up to about 150 bars. Preferably, the partial oxidation process is operated at a pressure in the range of from about 2 bars to about 125 bars, more preferably from about 5 bars to about 100 bars.

The partial oxidation process is also operable over a wide range of temperatures. At commercial scale, the feed is preferably contacted with the catalyst at high temperatures. In one embodiment, the feed mixture is contacted with the catalyst at a temperature in excess of 600° C. Preferably, the feed mixture is contacted with the catalyst at a temperature in the range of from about 600° C. to about 1,700° C., more preferably from about 800° C. to about 1,600° C. The feed mixture is preferably preheated prior to contacting the catalyst.

The feed is provided during the operation of the process at a suitable space velocity to form a substantial amount of CO in the product. In one embodiment, gas space velocities (expressed in normal liters of gas per kilogram of catalyst per hour) are in the range of from about 20,000 Nl/kg/hr to about 100,000,000 Nl/kg/hr, more preferably in the range of from about 50,000 Nl/kg/hr to about 50,000,000 Nl/kg/hr, and most preferably in the range of from about 500,000 Nl/kg/hr to about 30,000,000 Nl/kg/hr.

D. Combination Syngas Processes

Combination reforming processes can also be incorporated into this invention. Examples of combination reforming processes include autothermal reforming and fixed bed syngas generation. These processes involve a combination of gas phase partial oxidation and steam reforming chemistry.

The autothermal reforming process preferably comprises two synthesis gas generating processes, a primary oxidation process and a secondary steam reforming process. In one embodiment, a hydrocarbon feed stream is steam reformed in a tubular primary reformer by contacting the hydrocarbon and steam with a reforming catalyst to form a hydrogen and carbon monoxide containing primary reformed gas, the carbon monoxide content of which is further increased in the secondary reformer. In one embodiment, the secondary reformer includes a cylindrical refractory lined vessel with a gas mixer, preferably in the form of a burner in the inlet portion of the vessel and a bed of nickel catalyst in the lower portion. In a more preferred embodiment, the exit gas from the primary reformer is mixed with air and residual hydrocarbons, and the mixed gas partial oxidized to carbon monoxides.

In another embodiment incorporating the autothermal reforming process, partial oxidation is carried out as the primary oxidating process. Preferably, hydrocarbon feed, oxygen, and optionally steam, are heated and mixed at an outlet of a single large coaxial burner or injector which discharges into a gas phase partial oxidation zone. Oxygen is preferably supplied in an amount which is less than the amount required for complete combustion.

Upon reaction in the partial oxidation combustion zone, the gases flow from the primary reforming process into the secondary reforming process. In one embodiment, the gases are passed over a bed of steam reforming catalyst particles or a monolithic body, to complete steam reforming. Desirably, the entire hydrocarbon conversion is completed by a single reactor aided by internal combustion.

In an alternative embodiment of the invention, a fixed bed syngas generation process is used to form synthesis gas. In the fixed bed syngas generation process, hydrocarbon feed and oxygen or an oxygen-containing gas are introduced separately into a fluid catalyst bed. Preferably, the catalyst is comprised of nickel and supported primarily on alpha alumina.

The fixed bed syngas generation process is carried out at conditions of elevated temperatures and pressures that favor the formation of hydrogen and carbon monoxide when, for example, methane is reacted with oxygen and steam. Preferably, temperatures are in excess of about 1,700° F. (927° C.), but not so high as to cause disintegration of the catalyst or the sticking of catalyst particles together. Preferably, temperatures range from about 1,750° F. (954° C.) to about 1,950° F. (1,066° C.), more preferably, from about 1,800° F. (982° C.) to about 1,850° F. (1,010° C.).

Pressure in the fixed bed syngas generation process may range from atmospheric to about 40 atmospheres. In one embodiment, pressures of from about 20 atmospheres to about 30 atmospheres are preferred, which allows subsequent processes to proceed without intermediate compression of product gases.

In one embodiment of the invention, methane, steam, and oxygen are introduced into a fluid bed by separately injecting the methane and oxygen into the bed. Alternatively, each stream is diluted with steam as it enters the bed. Preferably, methane and steam are mixed at a methane to steam molar ratio of from about 1:1 to about 3:1, and more preferably from about 1.5:1 to about 2.5:1, and the methane and steam mixture is injected into the bed. Preferably, the molar ratio of oxygen to methane is from about 0.2:1 to about 1.0:1, more preferably from about 0.4:1 to about 0.6:1.

In another embodiment of the invention, the fluid bed process is used with a nickel based catalyst supported on alpha alumina. In another embodiment, silica is included in the support. The support is preferably comprised of at least 95 wt % alpha alumina, more preferably at least about 98% alpha alumina, based on total weight of the support.

III. Syngas Feed to Slurry Bubble Reactor

Synthesis gas (syngas) is used in the feed to the slurry bubble reaction system of this invention. Desirably, the synthesis gas feed (including any recycle syngas recovered from the process itself as well as fresh syngas) has a molar ratio of hydrogen ($H_2$) to carbon oxides ($CO+CO_2$) in the range of from about 0.5:1 to about 20:1, preferably in the range of from about 1:1 to about 10:1. In another embodiment, the synthesis gas has a molar ratio of hydrogen ($H_2$) to carbon monoxide (CO) of at least 2:1. Carbon dioxide is optionally present in an amount of not greater than 50% by weight, based on total weight of the synthesis gas, and preferably less than 20% by weight, more preferably less than 10% by weight.

Desirably, the stoichiometric molar ratio is sufficiently high so as maintain a high yield of methanol, but not so high as to reduce the volume productivity of methanol. Preferably, the synthesis gas fed to the methanol synthesis process has a stoichiometric molar ratio (i.e., a molar ratio of ($H_2-CO_2$)/($CO+CO_2$)) of from about 1.0:1 to about 2.7:1, more preferably from about 1.5 to about 2.5, more preferably a stoichiometric molar ratio of from about 1.7:1 to about 2.5:1.

IV. Catalyst

Preferably, the methanol synthesis catalyst used in the process of this invention includes an oxide of at least one element selected from the group consisting of copper, silver, zinc, boron, magnesium, aluminum, vanadium, chromium, manganese, gallium, palladium, osmium and zirconium. More preferably, the catalyst is a copper based catalyst, more preferably in the form of copper oxide.

In another embodiment, the catalyst used in the methanol synthesis process is a copper based catalyst, which includes an oxide of at least one element selected from the group consisting of silver, zinc, boron, magnesium, aluminum, vanadium, chromium, manganese, gallium, palladium, osmium and zirconium. Preferably, the catalyst contains copper oxide and an oxide of at least one element selected from the group consisting of zinc, magnesium, aluminum, chromium, and zirconium. More preferably, the catalyst contains oxides of copper and zinc.

In yet another embodiment, the methanol synthesis catalyst comprises copper oxide, zinc oxide, and at least one other oxide. Preferably, the at least one other oxide is selected from the group consisting of zirconium oxide, chromium oxide, vanadium oxide, magnesium oxide, aluminum oxide, titanium oxide, hafnium oxide, molybdenum oxide, tungsten oxide, and manganese oxide.

In various embodiments, the methanol synthesis catalyst comprises from about 10 wt % to about 70 wt % copper oxide, based on total weight of the catalyst. Preferably, the methanol synthesis contains from about 15 wt % to about 68 wt % copper oxide, and more preferably from about 20 wt % to about 65 wt % copper oxide, based on total weight of the catalyst.

In one embodiment, the methanol synthesis catalyst comprises from about 3 wt % to about 30 wt % zinc oxide, based on total weight of the catalyst. Preferably, the methanol synthesis catalyst comprises from about 4 wt % to about 27 wt % zinc oxide, more preferably from about 5 wt % to about 24 wt % zinc oxide.

In embodiments in which copper oxide and zinc oxide are both present in the methanol synthesis catalyst, the ratio of copper oxide to zinc oxide can vary over a wide range. Preferably in such embodiments, the methanol synthesis catalyst comprises copper oxide and zinc oxide in a Cu:Zn atomic ratio of from about 0.5:1 to about 20:1, preferably from about 0.7:1 to about 15:1, more preferably from about 0.8:1 to about 5:1.

V. Recovery and Further Processing of Methanol Product

The methanol product from the slurry bubble reactor is generally sent to a separation unit or vessel to remove light product having a higher boiling point than the methanol. This separation preferably yields a liquid product rich in methanol, although the separated methanol product can include other components such as water. The separated methanol product can be used "as is," or it can be further processed if desired. Processing can be accomplished using any conventional means. Examples of such means include distillation, selective condensation, and selective adsorption. Process conditions, e.g., temperatures and pressures, can vary according to the particular methanol composition desired. It is particularly desirable to minimize the amount of water and light boiling point components in the methanol composition, but without substantially reducing the amount of methanol present.

In one embodiment, the separated and recovered methanol product is sent to a let down vessel so as to reduce the pressure to about atmospheric or slightly higher. This let down in pressure allows undesirable light boiling point components to be removed from the methanol composition as a vapor. The vapor is desirably of sufficient quality to use a fuel.

In another embodiment, the separated recovered methanol product is sent from the methanol synthesizing unit or vessel to a distillation system. The distillation system contains one or more distillation columns which are used to further separate the desired methanol composition from water and hydrocarbon by-product streams. Desirably, the methanol composition that is separated from the crude methanol comprises a majority of the methanol contained in the methanol product prior to separation.

In one embodiment, the distillation system includes a step of treating the recovered methanol product steam being distilled so as to remove or neutralize acids in the stream. Preferably, a base is added in the system that is effective in neutralizing organic acids that are found in the methanol stream. Conventional base compounds can be used. Examples of base compounds include alkali metal hydroxide or carbonate compounds, and amine or ammonium hydroxide compounds. In one particular embodiment, about 20 ppm to about 120 ppm w/w of a base composition, calculated as stoichiometrically equivalent NaOH, is added, preferably about 25 ppm to about 100 ppm w/w of a base composition, calculated as stoichiometrically equivalent NaOH, is added.

Examples of distillation systems include the use of single and two column distillation columns. Preferably, the single columns operate to remove volatiles in the overhead, methanol product at a high level, fuel oil as vapor above the feed and/or as liquid below the feed, and water as a bottoms stream.

In one embodiment of a two column system, the first column is a "topping column" from which volatiles are taken overhead and methanol liquid as bottoms. The second is a "rectifying column" from which methanol product is taken as an overhead stream or at a high level, and water is removed as a bottoms stream. In this embodiment, the rectifying column includes at least one off-take for fuel oil as vapor above the feed and/or as liquid below the feed.

In another embodiment of a two column system, the first column is a water-extractive column in which there is a water feed introduced at a level above the crude methanol feed level. It is desirable to feed sufficient water to produce a bottoms liquid containing over 40% w/w water, preferably 40% to 60% w/w water, and more preferably 80% to 95% w/w water. This column optionally includes one or more direct fuel oil side off-takes.

In yet another embodiment, the distillation system is one in which an aqueous, semi-crude methanol is taken as liquid above the feed in a single or rectifying column. The semi-crude methanol is passed to a rectifying column, from which methanol product is taken overhead or at a high level. Preferably, water or aqueous methanol is taken as a bottoms stream.

Alternatively, undesirable by-products are removed from the separated methanol stream from the methanol synthesis reactor by adsorption. In such a system, other components such as fuel oil can be recovered by regenerating the adsorbent.

VI. Use of the Methanol Composition in the Manufacture of Olefins

The methanol product composition of this invention can be used as feed for any conventional process. Examples of such uses include the manufacture of methyl tertiary butyl alcohol (MTBE) for use in reformulated gasolines and oxygenated fuels, the use of methanol as a fuel for fuel cells, use as feedstock to make olefins, and for use in making acetic acid and formaldehyde.

The methanol product stream of this invention is particularly suited for conversion to olefins, particularly ethylene and/or propylene. The methanol product stream can be fed directly to an olefin conversion process or it can be transported in large quantities over great distances and converted to olefins.

According to this invention, the methanol product can be produced in large scale quantities for conversion to olefins, which is of great advantage for further conversion of the olefins to polyolefins such as polyethylene and polypropylene. Advantageously, this invention allows for at least 100,000 metric tons of methanol product per year. Preferably, production is at least 500,000 metric tons per year, more preferably at least 1 million metric tons per year, and most preferably at least 2 million metric tons per year.

In one embodiment, the methanol stream of the invention is separated from a crude methanol stream, and transported to a location geographically distinct from that where the methanol composition was separated from the crude methanol stream. Preferably, the methanol composition of this invention is loaded into a vessel, and the vessel is transported over a body of water to a storage facility. The methanol can be easily transported at least 100, 500 or 1,000 miles or more. Once arriving at the storage facility, the methanol composition is delivered to a storage tank. From the storage tank, the methanol composition is ultimately sent to an olefin conversion unit for conversion to an olefin product. The methanol composition is preferably, loaded onto a ship, with the ship able to contain at least 20,000 tons, preferably at least 40,000 tons, and more preferably at least 80,000 tons.

An advantage of being able to transport the methanol composition is that the units which produce the methanol do not have to be located in close geographic proximity to the olefin conversion unit. This makes it possible to use remote gas reserves. These remote gas reserves would be used as feed for the methanol manufacturing facility. The methanol made at these remote sites can then be easily transported to a suitable location for conversion to olefins. Since olefins and polyolefins (i.e., plastics) demands are typically low at the remote gas sites, there will generally be a desire to transport methanol to high olefins and plastic demand areas. Methanol is routinely transported in vessels that are similar to those that transport crude oil and other fuels. Examples of locations of remote gas reserves include the coastline of west Africa, northwest Australia, in the Indian Ocean, and the Arabian Peninsula. Examples of locations of preferred sites to convert methanol to other products such as olefins include the U.S. Gulf coast and northwest Europe.

VII. Example of One Type of Embodiment of the Overall Invention

One example of a slurry bubble reactor system according to this invention is shown in FIG. 1. According to the embodiment in FIG. 1, syngas is sent by way of lines 10 and 11 to a slurry bubble reactor 12. The syngas is bubbled up through the reactor 12 and methanol is formed.

Vapor, which contains methanol product, exits the reactor 12 by way of a line 14. The vapor flows through a heat exchanger 16 to cool the relatively hot vapor.

The cooled product flows through a line 18 to a separator 20. Liquid methanol product is removed from the separator 20 by way of a line 22, and vapor is removed by way of a line 24. The vapor contains unreacted carbon monoxide, carbon dioxide and hydrogen, as well as other compounds that have a higher boiling point than the methanol.

A portion of the separated vapor is removed from the line 24 by way of a line 26 and purged from the system. The remainder of the vapor is sent to a compressor and then to a line 30 that is used as a recycle line. The vapor in the line 30 is combined with the syngas in the line 10 and the process continued.

The temperature and pressure of the reactor 12 are kept at the appropriate levels so that no external cooling is needed in this exothermic reaction process. The pressure and temperature can be controlled as the desired level by controlling the amount of syngas input to the reactor 12, as well as controlling the amount of syngas vapor recycled through line 30. The temperature of the syngas in line 10 or the syngas recycle in line 30 can be controlled as well so as to control the temperature the reactor 12. This can be done, for example, by adding a heat exchanger to one or both of lines 10 and 30 to cool the gases flowing through those lines.

This process was simulated using PRO/II ver. 6.0 software, with a capacity based on 100 kg-mole/hr of synthesis gas. The corresponding material balance information is shown in Table 1.

TABLE 1

| Steam No. and Description | 10 Makeup Syngas | 11 Reactor Feed | 14 Reactor Effluent | 18 Cooled Reactor Effluent | 24 Separator Vapor | 26 Purge Gas | 30 Recycle Syngas | 22 Methanol Product |
|---|---|---|---|---|---|---|---|---|
| Phase | Mixed | Mixed | Vapor | Mixed | Vapor | Vapor | Vapor | Liquid |
| Temperature (° C.) | 48.0 | 47.2 | 212.2 | 48.0 | 48.0 | 48.0 | 48.0 | 48.0 |
| Pressure (bar) | 45.0 | 45.0 | 45.0 | 45.0 | 45.0 | 45.0 | 45.0 | 45.0 |
| Flowrate (kg-mol/hr) | 100.0 | 500.1 | 441.4 | 441.4 | 408.8 | 8.8 | 400.0 | 32.6 |
| Molar Composition (%) | | | | | | | | |
| $H_2O$ | 0.34 | 0.10 | 0.53 | 0.53 | 0.03 | 0.03 | 0.03 | 6.67 |
| $N_2$ | 2.01 | 17.69 | 20.04 | 20.04 | 21.62 | 21.62 | 21.62 | 0.26 |
| CO | 28.38 | 13.62 | 9.20 | 9.20 | 9.92 | 9.92 | 9.92 | 0.16 |
| $CO_2$ | 4.12 | 13.71 | 15.11 | 15.11 | 16.11 | 16.11 | 16.11 | 2.68 |
| $CH_4$ | 1.86 | 15.46 | 17.52 | 17.52 | 18.87 | 18.87 | 18.87 | 0.59 |
| $CH_3OH$ | 0.00 | 1.44 | 8.28 | 8.28 | 1.80 | 1.80 | 1.80 | 89.34 |
| $H_2$ | 63.28 | 37.98 | 29.32 | 29.32 | 31.64 | 31.64 | 31.64 | 0.29 |

The data in Table 1 show that the reaction process of this invention provides relatively high conversion of CO and $CO_2$ (21.5% per pass conversion; 90.1% overall conversion), without having to remove heat from the reactor.

The principles and modes of operation of this invention have been described above with reference to various exemplary and preferred embodiments. As understood by those of skill in the art, the overall invention, as defined by the claims, encompasses other preferred embodiments not specifically enumerated herein.

The invention claimed is:

1. A process for making a methanol product in a slurry bubble reactor, comprising:
    feeding syngas to a slurry bubble reactor, wherein the reactor has a liquid height to diameter ratio of not greater than 10:1; and
    contacting the syngas with methanol forming catalyst in the reactor at a superficial gas velocity of at least 0.05 m/sec to form methanol product, wherein the reactor is maintained at a pressure of not greater than 100 bar absolute and at an average reactor outlet temperature of not greater than 220° C., without applying external or internal cooling.

2. The process of claim 1, wherein the methanol product is continued to form in the reactor until conversion of carbon monoxide in the syngas is at least about 30%.

3. The process of claim 1, wherein the average reactor outlet temperature is controlled by adjusting the temperature of the feed entering the reactor.

4. The process of claim 3, wherein the syngas feed entering the reactor is maintained at an average temperature of not greater than 90° C.

5. The process of claim 1, wherein the reactor is maintained at a pressure of not greater than 60 bar absolute.

6. The process of claim 1, wherein the methanol product contains unreacted synthesis gas components, and at least some of the synthesis gas components are separated from the methanol into a concentrated liquid methanol product and a vapor product.

7. The process of claim 6, wherein the separated synthesis gas components are purged, recycled back to the reactor, or a combination of both.

8. The process of claim 6, wherein at least a portion of the separated synthesis gas components are recycled back to the reactor at a temperature or volume flow rate to control or maintain the reactor at the reactor outlet temperature.

9. The process of claim 1, wherein the methanol forming catalyst includes an oxide of at least one element selected from the group consisting of copper, silver, zinc, boron, magnesium, aluminum, vanadium, chromium, manganese, gallium, palladium, osmium and zirconium.

10. The process of claim 1, wherein the reactor has a temperature differential between the reactor outlet and the reactor outlet of not greater than 50° C.

11. A process for controlling average reactor outlet temperature in a process for making methanol product in a slurry bubble reactor, comprising:
    feeding syngas to a slurry bubble reactor, wherein the reactor has a liquid height to diameter ratio of not greater than 10:1;
    contacting the syngas with methanol forming catalyst in the reactor at a superficial gas velocity of at least 0.05 m/sec to form methanol product;
    separating at least a portion of unreacted synthesis gas components from the methanol product into a concentrated liquid methanol product and a vapor containing syngas; and
    recycling at least some of the vapor containing the syngas back to the reactor at a temperature or volume flow rate to control or maintain the reactor at a predetermined average reactor outlet temperature of not greater than 220° C. and at a pressure of not greater than 100 bar absolute, and wherein the reactor is operated without applying external or internal cooling.

12. The process of claim 11, wherein the methanol product is continued to form in the reactor until conversion of carbon monoxide in the syngas is at least about 30%.

13. The process of claim 11, wherein the average reactor outlet temperature is further controlled by adjusting the temperature of the feed entering the reactor.

14. The process of claim 13, wherein the syngas feed entering the reactor is maintained at an average temperature of not greater than 90° C.

15. The process of claim 11, wherein the reactor is maintained at a pressure of not greater than 60 bar absolute.

16. The process of claim 11, wherein the methanol forming catalyst includes an oxide of at least one element selected from the group consisting of copper, silver, zinc, boron, magnesium, aluminum, vanadium, chromium, manganese, gallium, palladium, osmium and zirconium.

17. The process of claim 11, wherein the reactor has a liquid height to diameter ratio of not greater than 5:1.

18. The process of claim 17, wherein the syngas is contacted with the methanol forming catalyst in the reactor at a superficial gas velocity of at least 0.1 m/sec to form methanol product.

* * * * *